United States Patent [19]

Jackson et al.

[11] Patent Number: 5,496,533
[45] Date of Patent: Mar. 5, 1996

[54] RHENIUM COMPLEXES

[75] Inventors: Timothy W. Jackson, Cronulla, Australia; Masaharu Kojima, Morioka, Japan; Richard M. Lambrecht, Birchgrove, Australia

[73] Assignee: Australian Nuclear Science & Technology Organisation, New South Wales, Australia

[21] Appl. No.: 97,403

[22] Filed: Jul. 26, 1993

[30] Foreign Application Priority Data

Jul. 31, 1992 [AU] Australia .................. PL3882

[51] Int. Cl.$^6$ .................... A61K 51/04; A61K 51/12
[52] U.S. Cl. ............................................. 424/1.65
[58] Field of Search ............... 534/10; 424/1.65, 424/1.69, 1.29

[56] References Cited

U.S. PATENT DOCUMENTS

| | | | |
|---|---|---|---|
| 2,580,695 | 1/1952 | Niederhauser | 260/601 |
| 4,578,391 | 3/1986 | Kawata et al. | 514/256 |
| 4,925,650 | 5/1990 | Nosco et al. | 424/1.1 |
| 4,926,869 | 5/1990 | Rubin et al. | 128/654 |

OTHER PUBLICATIONS

Mahmood et al., "Stereoisomers of Neutral Oxotechnetium (V) and Oxorhenium (V) Complexes", *Technetium and Rhenium in Chemistry & Nuclear Medicine*, 3, Edited by M. Nicolini et al., 1990, pp. 119–124.

"Stereoisomers of neutral oxotechneitum(V) complexes", Manhood, et al *Technetium and Rhenium in Chemistry and Nuclear Medicine* 3 Edited by M. Nicholini et al (1990), pp. 119–124, Raven Press, New York.

"Effect of Arterial Administration of High-molecular weight Anticancer Agents SMANCS with Lipid Lymphographic Agent on Hepatoma: a Preliminary Report," Toshmitisu Konno, et al *Eur. J. Cancer Clin. Oncol.* 19 No. 8, 1983 pp. 1053–1065.

"Critical Evaluation of 1–131–Lipiodol Therapy for Hepatocellular Carcinoma", C. H. Park, H. S. Yoo and J. H. Suh. *Eur. J. Nucl. Med.*, 1990 16, S143.

"1–Alkyl–(or aryl–) amino–2–mehtylpropane–2–thiols. Some Bi– and Thetradentate Nitrogen–Sulfur Ligands from Schiff's Base Disulfides", James L. Cobrin, et al *J. Org. Chem.* 41 No. 3, 1976, pp. 489–491.

"Use of Oil Contrast Medium for Selective Drug Targeting to Tumor: Enhanced Theraputic Effect and X-Ray Image", Ken Iwai, et al *Cancer Research* 44, May 1984, pp. 2115–2121.

"Biodistribution and In Vivo Kinetics of Iodine–131 Lipiodol Infused via the Hepatic Artery of Patients with Hepatic Cancer", Masayuki Nakajo, et al., *J. Nucl. Med.*, Jun. 1988, 29, No. 6 pp. 1066–1077.

"Transannular Cyclization of 1,2–Dithia–5, 8–diazacyclodera–4,8–dienes during Borohydrige Reduction", Alummottil V. Joshua, et al, *J. Org. Chem.* 1987, 52, No. 12, pp. 2447–2451.

"Novel Synthesis of Aminoethanethiols", John J. D'Amico, et al *J. Org. Chem.* 1975 40, No. 9, pp. 1224–1227.

"Synthesis and Biodistribution of Neutral Lipid–Soluble Tc–99m Complexes that Cross the Blood–Brain Barrier", H. F. Kung, et al *J. Nucl. Med.* 1984, 25, No. 3, pp. 326–332.

"The Use of Diaminodithio for Labeling Small Molecules with Technetium–99m", F. H. Liang, et al *Nucl. Med. Biol.* 1987, 14 No. 1, pp. 63–67.

*Primary Examiner*—Shean Wu
*Assistant Examiner*—Lara E. Chapman
*Attorney, Agent, or Firm*—James W. Kayden; Hopkins & Thomas

[57] ABSTRACT

Rhenium complexes of formula (I), radiolabelled complexes thereof or pharmaceutically acceptable salts thereof:

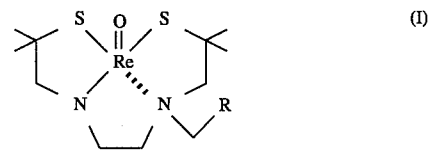

wherein R is straight or branched chain $C_{1-10}$ alkyl, $C_{1-10}$ alkenyl, $C_{1-10}$ alkynyl optionally substituted by cycloalkyl or aryl; $C_{1-10}$ cycloalkyl optionally substituted by straight or branched chain alkyl, alkenyl, alkynyl or aryl; or aryl optionally substituted by straight or branched chain alkyl, alkenyl, alkynyl or cycloalkyl for use in liver cancer therapy and metastasis of cancer.

21 Claims, No Drawings

RHENIUM COMPLEXES

This invention relates to Rhenium complexes and in particular to radiolabelled Rhenium complexes for use in radiotherapy of tumours.

The radioactive isotopes of Rhenium, Rhenium-186 and Rhenium-188 share similar periodic group chemical properties with technetium. Rhenium-186 has a 90.6 hour half-life and decays by beta emission of endpoint energy of 1.07 MeV. It is produced by neutron irradiation of Rhenium-185. Rhenium-188 has a half-life of 17.0 h and decays by beta emission of endpoint energy of 2.12 MeV. It can be produced in no-carrier added form by the double neutron capture reaction on Tungsten-186 to form Tungsten-188 with a half-life of 69 days which decays to rhenium-188. $^{188}$Re can be obtained by the $^{188}$W→$^{188}$Re generator. $^{186}$Re is reactor made from $^{185}$Re metal target.

Both Rhenium-186 and -188 decay by gamma emissions which can be detected with nuclear medicine instruments. For radioimmunotherapy, however, radiorhenium is demanded in high specific activity because of the nature of binding of antibody to tumour cells. Accordingly, $^{188}$Re of high specific activity is preferred for radioimmunotherapy with monoclonal antibodies. On the other hand, $^{186}$Re also has applications for internal radiotherapy where receptor specific interactions do not limit medical applications by delivery of lower specific activity Re-compounds.

Iwai, et al., (1984) has reported radiotherapy of liver cancer using $^{131}$I-labelled LIPIODOL. LIPIODOL is a tradename of Laboratoire Guerbet, Paris, France The lipid contrast medium Lipiodol, which is an iodinated poppyseed oil (38% iodine [w/w] with a specific gravity of 1.3) used as a lymphographic agent, was retained almost selectively in the tumour tissue when injected into the tumour feeding artery. Nakajo et al. (1988) reported the biodistribution and in vivo kinetics of [$^{131}$I]Lipiodol infused into hepatic artery, and estimated the potential of internal radiotherapy of hepatic cancer in five patients treated during 1986 to 1990 (Park et al., 1990). The authors concluded that: the smaller the vascular tumour, the better the response; large tumours (>4.5 cm) were treated more effectively by a combination of $^{131}$I-Lipiodol and intra-arterial chemotherapy, embolization or hyperthermia. Although the mechanism of the selective accumulation of Lipiodol is not fully understood as yet, the combination of Lipiodol with an anticancer agent permits enhanced interatomic drug concentration. SMANCS is an anticancer agent, which has a molecular weight of about 15,000 daltons. SMANCS is a lipophilic derivative of neocarzinostatin (NCS), which is an anti-tumor antibiotic, and a synthetic water-soluble polymer [(styrene)$_{1-3}$(maleic acid$_{4-7}$/anhydride$_1$)] (SMA). A homogeneous suspension of SMANCS in Lipiodol has been used for arterial administration (Konno et al., 1983). The chemotherapy with SMANCS-Lipiodol showed marked anti-tumour effect by survival period and histological observation.

$^{131}$I-Lipiodol or the Lipiodol-anticancer agent combination has shown remarkable effectiveness for liver cancer therapy. The use of $^{131}$I for the labelling of Lipiodol has shown that the $^{131}$I nuclide suffers substantially from several undesirable physical and biological properties, principally the rapid and persistent in vivo dehalogenation. The beta emission of $^{131}$I has an endpoint energy of 0.32 MeV. Accordingly, we have synthesised $^{186}$Re or $^{188}$Re labelled complexes for use in combination with Lipiodol as a useful tool for internal radiotherapy of liver cancer. For the purposes, the $^{186}$Re and $^{188}$Re compound must be soluble in Lipiodol and stable.

In one aspect, the present invention provides Rhenium complexes of formula (I), radiolabelled complexes thereof or pharmaceutically acceptable salts thereof:

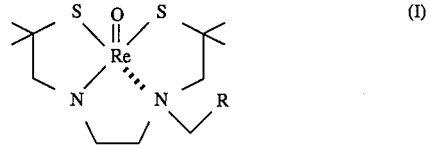

wherein R is straight or branched chain $C_{1-10}$ alkyl, $C_{1-10}$ alkenyl, $C_{1-10}$ alkynyl optionally substituted by cycloalkyl or aryl; $C_{1-10}$ cycloalkyl optionally substituted by straight or branched chain alkyl, alkenyl, alkynyl or aryl; or aryl optionally substituted by straight or branched chain alkyl, alkenyl, alkynyl or cycloalkyl.

Preferably, R is —(CH$_2$)$_4$CH$_3$, —(CH$_2$)$_6$CH$_3$ or —(CH$_2$)$_8$CH$_3$.

In another aspect, the present invention provides a method of preparing compounds of formula (I), radiolabelled complexes thereof or pharmaceutically acceptable salts thereof, where R is straight or branched chain $C_{1-10}$ alkyl, $C_{1-10}$ alkenyl, $C_{1-10}$ alkynyl optionally substituted by cycloalkyl or aryl; $C_{1-10}$ cycloalkyl optionally substituted by straight or branched chain alkyl, alkenyl, alkynyl or aryl; or aryl optionally substituted by straight or branched chain alkyl, alkenyl, alkynyl or cycloalkyl which comprises the steps of (a) (i) treating 1,1,4,4-tetramethylimidazolidino[1,2-d] dithiaazepine with an acylating agent to provide the acyl derivative;

(ii) treating the acyl derivative with a reducing agent to provide of 2,2,9,9-tetramethyl-4,7-diaza- 1,10-decanethiol (N—CH$_2$—R TMDADT) and (iii) treating the N—CH$_2$—R TMDADT derivative with a rhenium agent in the presence of stannous chloride to produce compounds of formula (I); or (b) (i) treating 1,1,4,4-tetramethylimidazolidino[1,2-d] dithiaazepine with the desired α-bromoalkane followed by (ii) treating the resultant N-alkyl compound with a reducing agent and (iii) treating the resulting N-alkylTMDADT derivative with a rhenium agent in the presence of stannous chloride to produce compounds of formula (I).

The synthesis route of Re═O[4—N—CH$_2$—R] is shown in scheme 1. Treatment of (1) with an acylating agent such as acylchloride gave N-acyl compounds (3) in good yield. The reduction of (3) with a reducing agent such as LiAlH$_4$ afforded N—CH$_2$—R compounds (4) in 40–50% yield. Treatment of compounds (4) with ReO$_4^-$ yielding agents such as NH$_4$ReO$_4$ in stannous chloride provides complexes of formula (I).

The Re═O[N-n-hexylTMDADT] was crystallized and dissolved in Lipiodol to more than 10 mg/1 ml and the solution showed high chemical stability. The $^{186}$Re═O[N-n-hexylTMDADT] which is expected as a radiopharmaceutical for liver cancer therapy was also obtained in good yield.

In a further aspect, the present invention provides rhenium complexes of formula (I), radiolabelled complexes thereof or pharmaceutically acceptable salts thereof as radiopharmaceuticals for liver cancer therapy and metastasis of cancer.

Among the Re═O(V)[DADT] complexes made, we have found that 2,2,9,9-tetramethyl-4-N-alkyl-4,7-diaza-1,10-decanedithiol (4) (alkyl=Me to decanyl) makes stable and Lipiodol soluble Re═O[4-N-alkylTMDADT]. The synthesis route of Re═O[4-N-methyl] is shown in Scheme 2.

1,1,4,4-tetramethylimidazolidino[1,2 -d]dithiaazepine (1) was obtained in 94% yield by the reduction of 3,3,10,10-tetramethyl-1,1-dithia-5,8-diazacyclodeca-4,8-diene using one molar ratio of sodium borohydride under

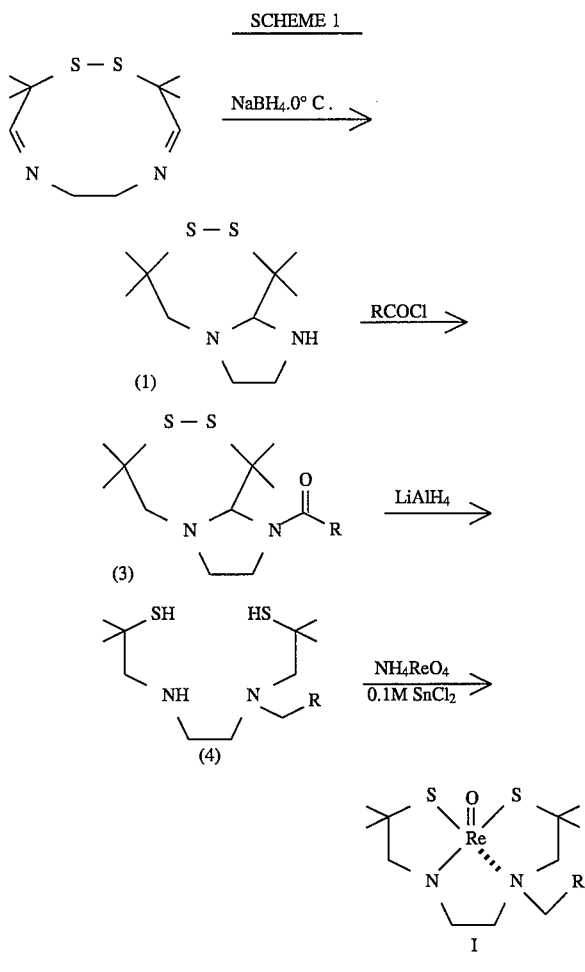

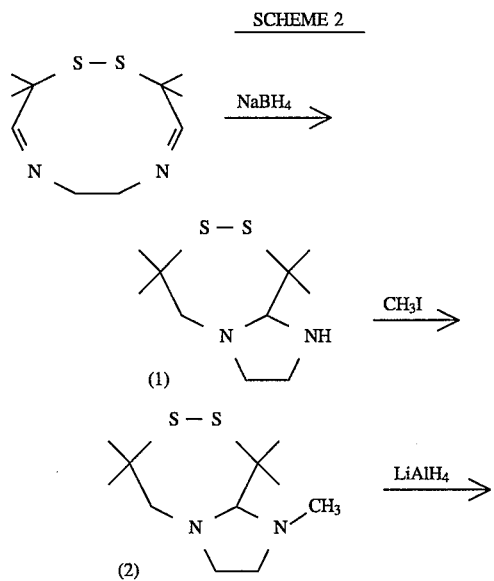

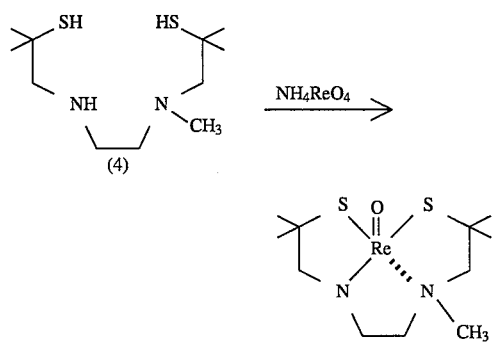

cooling in an ice bath. Iodomethylation of (1) following neutralization with sodium hydroxide gave N-methyl compound (2). Reduction of (2) with LiAlH$_4$ afforded N-methyl compound (4) in 40–50% yield. As the HCl salts obtained were very hygroscopic, rhenium complexes were made using unpurified HCl salts of (4) according to Mahmood's procedure (1990).

Synthesis of the Rhenium complexes of formula (I) may be also achieved using a modification of Scheme 2. In this method an α-Bromo.alkane of the appropriate length can be reacted with the intermediate (1) to form a long chain (C$_{2-10}$) N-alkyl compound which is readily reduced to the diaminedithiol ligand using LiAlH$_4$. This method allows easier and faster reduction step which in turn allows for purer and more stable ligands.

The solubility of the $^{186}$Re=O[4-N-n-hexyl TMDADT] in Lipiodol is sufficient to deliver a therapeutic dose within a single standard Lipiodol injection, typically 4– 5 ml (Konno et al., 1983; Nakajo et al., 1988). It is anticipated that the higher energy beta emission of $^{186}$Re (1.07 MeV) and its higher rate of retention in the tumour tissue as compared to [$^{131}$I]Lipiodol (0.32 MeV) will improve markedly the efficacy of radionuclide/Lipiodol therapy.

Therefore, in yet another aspect, the present invention provides radiolabelled rhenium complexes of formula (II), or pharmaceutically acceptable salts thereof

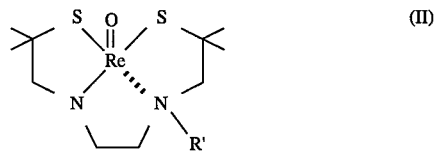

where R' is as defined for R in formula (I), in Lipiodol or other lipid soluble oils, long chain fatty acids or esters thereof.

Preferably, the other lipid soluble oils are grape seed oil, mustard seed oil, olive oil and the like. Esters include glycerides and ETHIODOL which is the ethyl ester of iodinated fatty acid of poppyseed oil. ETHIODOL is a tradename of Andre-Gelbe Laboratories, France.

In yet another aspect, the present invention provides the use of a radiolabelled rhenium complex of formula (II) to enhance the efficacy of Lipiodol in the treatment of liver cancer.

Formulations of the rhenium complex and oil combination are prepared and administered according to standard techniques. By way of example, about 5–10 mg of $^{186}$ReO [N-n-hexylTMDADT] of 20–40 mCi/mg summing to a dosage of approximately 200 mCi dissolved in a single standard Lipiodol injection (4–5 ml) i.e. a concentration of typically not more than 2.5 mg/ml is administered. The effective amount of the complex or the combination of the complex and Lipiodol required for use in the above conditions will vary both with the route of administration, the condition under treatment and the host undergoing treatment, and is ultimately at the discretion of the physician.

Complexes of formula (I) or (II) additionally synthesised with linker arms are useful for linking to monoclonal antibodies and radioimmunospecific pharmaceuticals to treat various cancers. As a result of the solubility of complexes of formula (II) in Lipiodol or other lipid soluble oils it has emerged that a combination of a complex of formula (II) with Lipiodol and other anticancer drugs such as SMANCS would be suitable for use in cancer therapy. A preferred use is the administration of the radioactive complex of formula (II) dissolved in Lipiodol via intra-arterial infusion into the liver as practised in the art of medicine.

A further preferred use of compounds of formula (II) is in the treatment of liver cancer, hepatoma and cancer metastasis to the liver resulting from cancer elsewhere in the body such as the colon.

No-carrier added $^{188}$Re is preferred to $^{186}$Re if the chelate is to be attached to a monoclonal antibody and administration in solution in addition to Lipiodol.

In yet another aspect, the present invention provides a pharmaceutical formulation comprising a compound of formula (I), a radio labelled compound thereof or a pharmaceutically acceptable salt thereof in a pharmaceutically acceptable carrier.

A pharmaceutical formulation of the present invention comprises the active compound together with one or more pharmaceutically acceptable carriers and optionally any other therapeutic ingredient. The formulation may conveniently be prepared in unit dosage form and may be prepared according to conventional pharmaceutical techniques. Additionally, the formulations may include one or more accessory ingredients, such as diluents, buffers, flavouring agents, binders, disintegrants, surface active agents, thickeners, lubricants, preservatives and the like.

The present invention also envisages complexes of formula (I) or (II) and their use in cancer therapy wherein the Rhenium is replaced by other radionuclides such as $^{99m}$Tc and radiotherapeutic isotopes such as $^{90}$Y. $^{90}$Y is reactor produced and decays by beta emission of endpoint energy of 2.27 MeV and has a half-life of 64 hours.

Specific embodiments of the present invention are illustrated by the following examples. It will be understood, however, that the invention is not confined to specific limitations set forth in the individual examples.

EXAMPLES 2,2-dithio-bis(2-methylpropanal)

This compound was prepared originally by Niederhauser et al., (1952). After that, however, several modified procedures were reported (Merz et al., 1963; D'Amico et al, 1975; Corbin et al., 1976; Kung et al., 1984; Liang et al., 1987). We obtained the compound in 40–65% yield according to Liang's method.

3,3,10,10-tetramethyl-1,2-dithia-5,8-diazacyclodeca-4,8-diene

This cyclic diimine was prepared from 2,2'dithio-bis(2-methylpropanal) and ethylenediamine by Kung et al. (1984) and Liang et al. (1987). We synthesised this compound in 50–65% yield according to Liang's procedure.

1,1,4,4-tetramethylimidazolidino[1,2-d]dithiazepine (1)

This compound was synthesized according to a method of Joshua et al. (1987) with modification. A mixture of 4.60 g (20 mmole) of 3,3,10,10-tetramethyl-1,2-dithia-5,8-diaza-cyclodeca- 4,8-diene in 80 ml of ethanol was cooled in an ice bath. To this mixture was added 0.756 g (20 mmole) of NaBH$_4$ by portions under stirring. The mixture was stirred for 30 min at room temperature, and ethanol was removed by evaporation under reduced pressure. To the residue was added water, and undissolved solid was extracted with ether. The extract was washed with water and dried over sodium sulphate. After removing ether by evaporation under reduced pressure, 4.37 g (94.0% yield) of solid was obtained. mp 58°–62° C. This compound was used without purification for further synthesis.

1,1,4,4-tetramethyl-9-N-methylimidazolidino[1,2-d] dithiazepine (2)

To a solution of 4.85 g of 1,1,4,4-tetramethylimidazolidino[ 1,2-d]dithiazepine in 20ml of ethanol was added 1 g of methyliodide. The mixture was heated to reflux for 3 hr. After cooling, ether was added and 6.15 g of crystals was collected by filtration. mp 193°– 194° C. The crystals (5.0 g) obtained were suspended in 50 ml of ether and NaOH (0.6 g) added in 20 ml of H$_2$O, and stirred until all of the crystals dissolved in the ether. The ether layer was separated and washed with water. After drying the ether layer over sodium sulphate, ether was evaporated under reduced pressure to give 3.20 g of oil which crystallized. mp 28°–29° C., H$^1$NMR (CDCl$_3$) . Analytical Calcd for C$_{11}$H$_{22}$N$_2$S$_2$:C, 53.61; H, 9.00; N, 11.37. Found: C, 53.53; H, 9.13; N, 11.57.

2,2,9,9-pentamethyl-4-N-methyl-4,7-diaza-1,10-decanedithiol [4(N—Me)]

To a solution of N-methyl-bicyclic compound (2) (10 mmole) in dry THF (100–150ml) was added a large excess of LiAlH$_4$ (30 mmole), and the mixture was refluxed for about 24 hr. The reaction mixture was quenched with salt. NH$_4$Cl, and filtered. The contents of the funnel were washed with 100ml of CHCl$_3$ twice and the combined filtrate of THF and CHCl$_3$ was evaporated to dryness under reduced pressure. The residue was dissolved in ether (100 ml), and the hydrochloride salt was made by addition of ethanol—HCl and removal of organic solvent under reduced pressure. The crystallinity of the HCl salts was poor due to their strong hygroscopic nature.

2,2,9,9-pentamethyl-4-N-octyl-4,7-diaza-1,1,10-decanedithiol [4(N—Me)]

To 1 equivalent of (1) was added 1.5 equivalent of 1-Bromooctane in toluene. 2 equivalents of K$_2$CO$_3$ was also added. The reaction was refluxed for 24 hours after which time the toluene was evaporated, water added and the aqueous layer extracted with ether. Purification of the ether layer products was by column chromatography (silica gel dichloromethane eluant) yielded the product in 46.7% yield.

This material was then easily reduced to the diaminedithiol using three equivalents of LiAlH$_4$ in tetrahydrofuran refluxed for twelve hours.

General Procedure for Acylation—Preparation of 3

A solution of 1 equivalent of bicyclic compound (1) in ether and 1.2 equivalents sodium hydroxide (1N NaOH—$H_2O$) was mixed with stirring in an ice bath, and to that 1 equivalent of acyl chloride was added dropwise. Then the mixture was stirred for 30 min at room temperature. The ether layer was separated, washed with water and dried over sodium sulphate. After removal of ether, N-acyl diazepine was obtained.

(1) Treatment of 1 (3.85 g, 16.56 mmole) with n-hexanoyl chloride (2.4 g, 17.5 mmole) gave an oily compound. After purification by silica gel column chromatography ($CHCl_3$), 5.0 g (91.1%) of the N-n-hexanoyl compound was obtained. The HCl salt was colourless silky needles, mp 133°–135° C. IR 1656 $cm^{-1}$ NMR (free base).

(2) Treatment of 1 (2.32 g, 10 mmole) with n-octanoyl chloride (1.63 g, 10 mmole) gave an oily compound. After purification by silica gel chromatography ($CHCl_3$), 2.86 g (79.7%) of the N-n-octanoyl compound was obtained. The HCl salt was colourless silky needles, mp 127°–128° C. IR 1653 $cm^{-1}$.

(3) Treatment of 1 (2.32 g, 10 mmole) with decanoyl chloride (1.94 g, 10 mmole) gave 3.88 g of oily compound. After purification by silica gel chromatography ($CHCl_3$), 3.03 g (78.4%) of N-decanoyl compound was obtained as a solid. mp 53°–56° C. IR 1651 $cm^{-1}$.

(4) Treatment of 1 (2.32 g, 10 mmole) with myristoyl chloride (2.72 g, 10 mmole) gave 4.41 g of solid compound. After purification by silica gel chromatography ($CHCl_3$), 2.0 g (45.2%) of N-myristoyl compound was obtained as a solid. mp 73°–74° C. IR 1651 $cm^{-1}$.

General Procedure for the Preparation of N-alkyl-2,2,9,9-tetramethyl-4,7-diaza-4-alkyl-1,10-decanedithiol (4)

To a solution of N-acyl-bicyclic compound (3) (10 mmole) in dry tetrahydrofuran (THF) (100–150ml) was added a large excess of $LiAlH_4$ (50 mmole), and the mixture was refluxed for about 24 hr. The reaction mixture was quenched with satd. $NH_4Cl$, and filtered. The contents of the funnel were washed with 100 ml of $CHCl_3$ twice and the combined filtrate of THF and $CHCl_3$ was evaporated to dryness under reduced pressure. Water was added (100 ml), and the pH was adjusted to 3.0 with concentrated HCl. The mixture was extracted with diethyl ether (80 ml/extraction) to remove ether soluble impurities. These ether solutions were discarded. The pH was then adjusted to 8.0 and extracted with fresh ether. These ether solutions were dried ($Na_2SO_4$), filtered and evaporated under reduced pressure. The residue was dissolved in ether (100 ml), and the hydrochloride salt was made by addition of ethanol—HCl and the organic solvent removed under reduced pressure. The crystallinity of the HCl salts was poor due to their very strong hygroscopic nature.

(1) 2,2,9,9-tetramethyl-4,7-diaza-4-n-hexyl-1,10-decanedithiol was obtained as oil in 45% yield.

ReO [N-n-Hexyl TM DADT]

$^1$H NMR ($CDCl_3$) δ0.9 (t, 3H), 1.3–1.4 (m, 6H), 1.5 (s, 3H), 1.6 (s, 3H), 1.8 (s, 3H), 1.85–1.90 (m, 2H), 1.90 (s, 3H), 2.2 (d, 1H), 2.4 (m, 1H), 3.2 (m, 1H), 3.25 (d, 1H) 3.5 (m, 2H) 3.8– 3.9 (m, 2H), 4.0 (m, 1H), 4.2 (m, 1H).

UV Maxima 370, 269 nm; IR (Re=O) 942 $cm^{-1}$; mp 120° C.

Analysis: Found(Calc)C, 37.2 (37.0); H, 6.8 (6.4); N, 5.2(5.4).

(2) 2,2,9,9-tetramethyl-4,7-diaza-4-n-octyl-1,10-dedcanedithiol was obtained as oil in 57.6% yield.

ReO [N-Octyl TM DADT]—$^1$H NMR ($CDCl_3$) δ0.9 (t, 3H), 1.2–1.4 (m, 8H), 1.5 (s, 3H), 1.6 (s, 3H), 1.8 (s, 3H), 1.80–1.90 (m, 2H), 1.9 (s, 3H), 2.2 (d, 1H), 2.3–2.4 (m, 1H), 3.1–3.2 (m, 1H), 3.2 (d, 1H), 3.4–3.55 (m, 2H), 3.8–3.9 (m, 2H), 3.9–4.0 (m, 1H), 4.1–4.2 (m, 1H), IR(Re=O) 941 $cm^{-1}$.

Preparation of Re=O[4-N-alkyl DADT]

These Rhenium complexes were prepared according to Mahmood's method (1990).

The ligand and $NH_4ReO_4$ were mixed in equimolar ratios in 50:50 aqueous ethanol. As the solution stirred, an equivalent amount of the stannous chloride solution [$SnCl_2$—$2H_2O$(0.1M) was prepared in HCl (0.9M)] was added dropwise. Addition of the reducing agent was accompanied by an instantaneous colour change to green-violet. The reaction mixtures were allowed to stir at room temperature for 10 min, after which the ethanol was evaporated under vacuum at room temperature. The reaction mixture was neutralized with $K_2CO_3$ and then extracted with chloroform. Following evaporation of the solvent the crude product was chromatographed on a silica gel column using chloroform as the eluting solvent. Only a deep violet band was eluted, which was collected and concentrated under reduced pressure.

General Procedure for Radiolabelling

1. Reaction of Ammonium Perrhenate with 2,2,9,9, tetramethyl-4,7-diamino,4-n-hexyl,1–10-decanedithiol (N Hexyl, TM-DADT)

250 mg of N-Hexyl TM DADT (freshly prepared (0.78 mmol)) and 209 mg of $NH_4ReO_4$ (0.78 mmol) (cold) were dissolved in 10 ml of EtOH and 10 ml of $H_2O$. To this was added 0.667 g (2.96 mmol) of $SnCl_2.2H_2O$ in 30 ml of 0.9M HCl.sol$^n$, freshly prepared and filtered through a 0.22 μm filter, over 15 minutes. The reaction was then stirred for two hours under nitrogen. The ethanol was removed in vacuo and the solution neutralised with concentrated $K_2CO_3$ solution. (pH 7–8). The aqueous layer was then extracted three times with chloroform (3× 20 ml).

The combined $CHCl_3$ extracts were then reduced in vacuo and chromatographed with column chromatography on Silica Gel G60 (Merck). The compound was isolated as a purple gum which was induced to crystallise in dichloromethane. Yield 120 mg (0.23 mmol) 29.5%

2. Reaction of Ammonium Perrhenate with 4,7-diamino, 4-n-octyl, 2,2,9,9-tetramethyl-1,10-decanedithiol: Dihydrochloride Salt (N-octyl TM DADT). 2HCl.

(1.42 mmol) 600 mg N-octylTM-DADT-2HCl and (1.42 mmol) 380 mg $NH_4ReO_4$, were dissolved in 20 ml of EtOH and 20 ml of water. To this was added 90 ml of 0.1M $SnCl_2.2H_2P$ solution in 0.9M HCl (freshly prepared and filtered). The reaction was allowed to run for 1 hour with stirring under $N_2$ gas. The ethanol was then removed in vacuo and the aqueous layer neutralised (pH 8) with solid $K_2CO_3$. The compound was then extracted with chloroform (100 ml×3) then the combined $CHCl_3$ extracts evaporated and the material chromatographed (column chromatography. Silica Gel G40 Merck) $CHCl_3$ eluant.

The compound was isolated as a purple gum—300 mg (39.8% yield).

3. Radiolabelling with $^{186}$Re

~3 mg of Re metal (10 mCi) was dissolved and oxidised with 30% $H_2O_2$ (2 ml) over 2 hours then 2 ml $NH_3$ 27% added to neutralise and form the ammonium perrhenate salt. The solution was then evaporated to dryness, washed with 2 ml of $H_2O$ into another flask and 2 ml of EtOH added with 30 mg of N-Hexyl TM DADT. 2HCl (78 μmol) and 3 ml of 0.1M $SnCl_2.2H_2O$) (90 mmol) in 0.9M HCl was slowly added. (The solution was filtered through 0.22 μm filter and freshly prepared). The reaction was allowed to proceed under $N_2$ for 2 hours, then removed and the ethanol removed in vacuo. The aqueous layer was neutralised with concentrated $K_2CO_3$ solution (≈2 ml) and extracted with $CHCl_3$ (3×5 ml).

The next day the combined, $CHCl_3$ extracts were reduced to dryness in vacuo then redissolved and chromatographed in chloroform on a Merck G40 Silica Column. A faint purple band was collected and registered as 5 mCi.

The $CHCl_3$ was removed, then the material dissolved in 2 ml EtOH, filtered through millipore 0.22 μm filter and chromatographed by rapid t.l.c. (one peak $r_f=0.9$) in $CHCl_3$.

REFERENCES

1. J. L. Corbin and D. E. Work (1976), J. Org. Chem., 41, 489.
2. K. Iwai, H. Maeda and T. Konno (1984), Cancer Res., 44, 2115.
3. J. J. D'Amico and W. E. Dahl (1975), J. Org. Chem., 40, 1224.
4. A. V. Joshua, J. R. Scott, S. M. Sondhi, R. G. Ball and J. W. Lown (1987), J. Org. Chem., 52, 2447.
5. T. Konno, H., Maeda, K. Iwai, S. Tashiro, S. Maki, T. Morinaga, M. Mochaninaga, T. Hiraoka and I. Yokoyama 1983, Eur. J. Cancer Cli., Oncol., 19, 1053.
6. H. F. Kung, M. Molnar, J. Billings, R. Wicks and M. Blau (1984), J. Nucl. Med. 25, 326.
7. F. H. Liang, F. Virzi and D. J. Hnatowich (1987), Nucl. Med. Bio., 14, 63.
8. K. W. Merz and M. Specker (1963), Arch. Pharm., 296, 427.
9. A. Mahmood, K. E. Baidoo and S. Z. Lever in Technetium and Rhenium in Chemistry and Nuclear Medicine 3 Edited by M. Nicolini, G. Bandoli and U. Mazzi (1990 ), pp. 119, Raven Press, New York.
10. M. Nakajo, H. Kobayashi, K. Shimabukuro, K. Shirono, H. Sakata, M. Taguchi, N. Uchiyama, T. Sonoda and S. Shinohara (1988), J. Nucl. Med., 29, 1066.
11. W. D. Niederhauser (1952), U.S. Pat. No. 2,580,695.
12. C. H. Park, H. S. Yoo and J. H. Sue (1990), Eur. J. Nucl. Med., 16, 5143.

The claims defining the invention are as follows:

1. A product comprising a rhenium complex of formula (I):

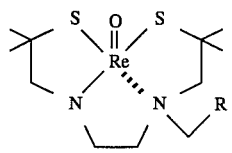

wherein the rhenium atom is radioactive, or a pharmaceutically acceptable salt wherein R is straight or branched chain $C_{1-10}$ alkyl, $C_{1-10}$ alkenyl, $C_{1-10}$ alkynyl optionally substituted by $C_{5-6}$ cycloalkyl or phenyl; $C_{5-6}$ cycloalkyl optionally substituted by straight or branched chain alkyl, alkenyl, alkynyl or phenyl; or phenyl optionally substituted by straight or branched chain alkyl, alkenyl, alkynyl or $C_{5-6}$ cycloalkyl; and a lipid soluble oil selected from the group consisting of iodized poppyseed oil.

2. A product according to claim 1 further comprising the anti-cancer agent SMANCS.

3. A product comprising a rhenium complex of formula (I):

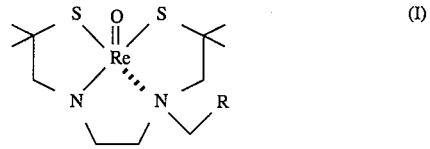

wherein the rhenium atom is radioactive, or a pharmaceutically acceptable salt thereof;

wherein R is straight or branched chain $C_{1-10}$ alkyl, $C_{1-10}$ alkenyl, $C_{1-10}$ alkynyl optionally substituted by $C_{5-6}$ cycloalkyl or phenyl; $C_{5-6}$ cycloalkyl optionally substituted by straight or branched chain alkyl, alkenyl, alkynyl or phenyl; or phenyl optionally substituted by straight or branched chain alkyl, alkenyl, alkynyl or $C_{5-6}$ cycloalkyl; and LIPIODOL (iodized poppyseed oil, 38% w/w iodine).

4. The product of claim 3, further comprising the anti-cancer agent SMANCS.

5. The product of claim 1, wherein R is straight or branched chain $C_5$, $C_7$, or $C_9$ alkyl.

6. A method of enhancing the efficacy of iodized poppy seed oil in the treatment of liver cancer in a subject which comprises administering to said subject a formulation containing a rhenium complex of formula (I):

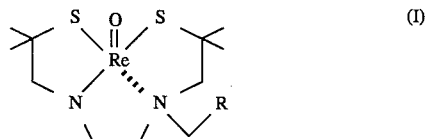

wherein the rhenium atom is radioactive, or a pharmaceutically acceptable salt thereof;

wherein R is straight or branched chain $C_{1-10}$ alkyl, $C_{1-10}$ alkenyl, $C_{1-10}$ alkynyl optionally substituted by $C_{5-6}$ cycloalkyl or phenyl; $C_{5-6}$ cycloalkyl optionally substituted by straight or branched chain alkyl, alkenyl, alkynyl or phenyl; or phenyl optionally substituted by straight or branched chain alkyl, alkenyl, alkynyl or $C_{5-6}$ cycloalkyl; and iodized poppyseed oil.

7. A method of treatment or prophylaxis of liver cancer and metastasis of cancer is a subject comprising administering to the subject a formulation containing a rhenium complex of formula (I):

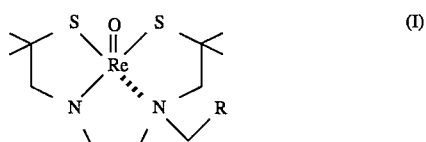

wherein the rhenium atom is radioactive, or a pharmaceutically acceptable salt thereof;

wherein R is straight or branched chain $C_{1-10}$ alkyl, $C_{1-10}$ alkenyl, $C_{1-10}$ alkynyl optionally substituted by $C_{5-6}$ cycloalkyl or phenyl; $C_{5-6}$ cycloalkyl optionally substituted by straight or branched chain alkyl, alkenyl, alkynyl or phenyl; or phenyl optionally substituted by straight or branched chain alkyl, alkenyl, alkynyl or $C_{5-6}$ cycloalkyl; and wherein the radioactive rhenium complex of formula (I) is administered in combination with iodized poppyseed oil.

8. A method according to claim 7 wherein the rhenium complex of formula (I) and iodized poppyseed oil are administered in combination with the anti-cancer agent SMANCS.

9. The method of claim 6, wherein R is straight or branched chain, $C_5$, $C_7$, or $C_9$ alkyl.

10. The method of claim 7, wherein R is straight or branched chain $C_5$, $C_7$, or $C_9$ alkyl.

11. The product of claim 1, wherein R is straight or branched chain $C_5$ alkyl.

12. The product of claim 2, wherein R is straight or branched chain $C_5$, $C_7$, or $C_9$ alkyl.

13. The product of claim 2, wherein R is straight or branched chain $C_5$ alkyl.

14. The product of claim 3, wherein R is straight or branched chain $C_5$, $C_7$, or $C_9$ alkyl.

15. The product of claim 3, wherein R is straight or branched chain $C_5$ alkyl.

16. The product of claim 4, wherein R is straight or branched chain $C_5$, $C_7$, or $C_9$ alkyl.

17. The product of claim 4, wherein R is straight or branched chain $C_5$ alkyl.

18. The method of claim 6, wherein R is straight or branched chain $C_5$ alkyl.

19. The method of claim 7, wherein R is straight or branched chain $C_5$ alkyl.

20. The method of claim 8, wherein R is straight or branched chain $C_5$, $C_7$, or $C_9$ alkyl.

21. The method of claim 8, wherein R is straight or branched chain $C_5$ alkyl.

* * * * *